United States Patent [19]

Mayer

[11] Patent Number: 5,449,912

[45] Date of Patent: Sep. 12, 1995

[54] MEASUREMENT CELL FOR WATER VAPOR SENSOR

[75] Inventor: William N. Mayer, White Bear Lake, Minn.

[73] Assignee: Modern Controls, Inc., Minneapolis, Minn.

[21] Appl. No.: 260,099

[22] Filed: Jun. 15, 1994

[51] Int. Cl.$^6$ .................................. G01N 21/61
[52] U.S. Cl. ........................ 250/343; 356/437; 356/440
[58] Field of Search ............ 250/343; 356/437, 440

[56] References Cited

U.S. PATENT DOCUMENTS 3,103,586  9/1963  Ovrebo .
3,174,037  3/1965  Demorest et al. .
3,902,068  8/1975  Wood .
5,146,283  9/1992  Parnoff et al. .................. 356/440

Primary Examiner—Carolyn E. Fields
Attorney, Agent, or Firm—Palmatier, Sjoquist & Helget

[57] ABSTRACT

An absorption cell of the type used to measure gas concentrations by pressure fluctuations of the concentrated gas in an IR radiation field, wherein the IR radiation through the field is affected by the pressurized gas fluctuations to thereby provide an electrical measurement of gas concentration. The sensitivity, linearity and accuracy of the measured gas concentration is improved by controlling the surface roughness of the interior walls of the measurement cell; the wall roughness is preferably controlled to between 15 and 70 microinches.

22 Claims, 6 Drawing Sheets

MEASUREMENT CELL FOR WATER VAPOR SENSOR

BACKGROUND OF THE INVENTION

This invention relates to an apparatus for measuring water vapor concentrations in a gas; or particularly the invention relates to the construction of a measurement cell for a water vapor sensor.

Instruments for measuring minute quantities of water vapor in a gas are well developed in the prior art. For example, U.S. Pat. No. 3,174,037, issued Mar. 16, 1965, discloses an apparatus and method for measuring the concentration of a gas in a mixture of gases, wherein the preferred embodiment relates to the measurement of water vapor in air. U.S. Pat. No. 3,902,068, issued Aug. 6, 1975, and owned by the assignee of the present invention, discloses a method and apparatus for measuring the quantity of a test gas such as butane which is present in an absorption cell. This patent relates to an apparatus for measuring the permeability of a membrane which is positioned to isolate the test gas cell from the absorption cell.

U.S. Pat. No. 5,390,536, issued Feb. 21, 1995, and owned by the assignee of the present invention, discloses a system for measuring water vapor permeability through a membrane, and utilizing the general principles of the '068 patent to measure the water vapor concentrations in an absorption cell.

All of the aforementioned patents utilize an infrared radiation source to generate radiation through windows into the absorption cell and the amount of this radiation which passes through the cell is monitored by an appropriate detector. U.S. Pat. No. 3,902,068 further utilizes a pumping apparatus for subjecting the gas in the absorption cell to pressure pulsations, thereby alternately increasing and decreasing the gas density in the absorption cell. The radiant energy passing through the cell is affected by the relative pressure fluctuations, leading to an output radiation signal which can be translated into an electrical alternating current output signal proportional to the gas concentration in the cell.

One of the problems in using an absorption cell of the aforementioned type is caused by undesired radiation signals which may result from heating effects of the absorption cell and/or internal reflections of the radiant energy within the cell. Therefore, the radiant energy signal which is passed through the cell via the windows in the cell includes a desired radiation signal plus an additional radiation signal which can be attributable to "noise" caused by the foregoing and perhaps other effects. In the prior art the measured water vapor concentrations were quite high, and therefore desired signal strength is sufficiently large so as to permit the noise component of the radiant energy signal to be filtered, while preserving an adequate amplitude of the desired signal. However, this limits the linearity of the instrument at water vapor permeation levels below about 10 grams per square meter per day (10 gm/$M^2$/day), and requires flow rate and other adjustments at extremely low levels of water vapor permeation; i.e., at levels below about 1 gm/$M^2$/day. Water vapor permeation below this level were inherently difficult, if not impossible, to measure. Extremely low levels of water vapor concentration will arise in an absorption cell when an instrument of the type described is used to test permeability of membranes having an inherent low water transmissivity characteristic. For example, films having a transmissivity of water vapor down to the range of approximately 10 grams per square meter per day (gm/$M^2$/day) can be readily measured in absorption cells of the type disclosed in the '068 patent without regard to the radiation noise component of the signal. However, recent technology advances in the manufacture of films such as coated films, produce transmissivity rates down to the range of under 0.01 gm/$M^2$/day, and such readings are severely affected by the aforementioned radiation noise components.

A significant problem which has been noted in attempting to use prior art absorption cells for measurements of extremely low water vapor permeation levels is the problem of nonlinearity. It has been noted that the measured radiation signal becomes nonlinear at 5 to 6 gm/$M^2$/day permeability measurements, and the usability of the instrument has thereby been diminished. The reasons for this nonlinear behavior are not fully understood and empirical testing has shown that the nonlinearity characteristic varies to some extent from instrument to instrument. These problems limit the usefulness of the prior art instruments for measuring some newly developed films.

SUMMARY OF THE INVENTION

The present invention comprises an improvement in the construction of an absorption cell of the aforementioned type wherein the noise component of radiation signals is controlled to permit accurate and linear transmissivity measurements at low levels which were unable to be achieved with prior art instruments. The radiation noise component is controlled such that the resultant signal caused by compression energy into the absorption cell and radiation noise in the absorption cell under dry gas conditions always produces a measured radiation signal which is in phase with radiation signals produced by any quantity of water vapor in the absorption cell. One technique for accomplishing this resultant signal is to construct the absorption cell in the form of a bore through a metallic block wherein the surface roughness of the bore is controlled to produce a roughened surface finish; where the surface finish is no less than about 15 microinches of roughness, as measured by the relative height of surface variations throughout the absorption cell. This has the effect of controlling the noise component of the radiation signal so as to eliminate the nonlinearities at relatively low permeability measurements.

It is the principal object of the present invention to provide an absorption cell of the aforementioned type wherein extremely low concentrations of water vapor in a gas can be detected accurately.

It is another object of the present invention to provide an absorption measurement cell with a linear transfer characteristic.

An advantage of the present invention is the simplicity of the construction of the aforementioned measurement absorption cell, wherein proper control of the surface finish within the cell permits the achievement of the desired results.

The invention will be best understood by reference to the following specification and claims, and with reference to the appended drawings.

DETAILED SPECIFICATION OF THE PREFERRED EMBODIMENT

Figure 2:
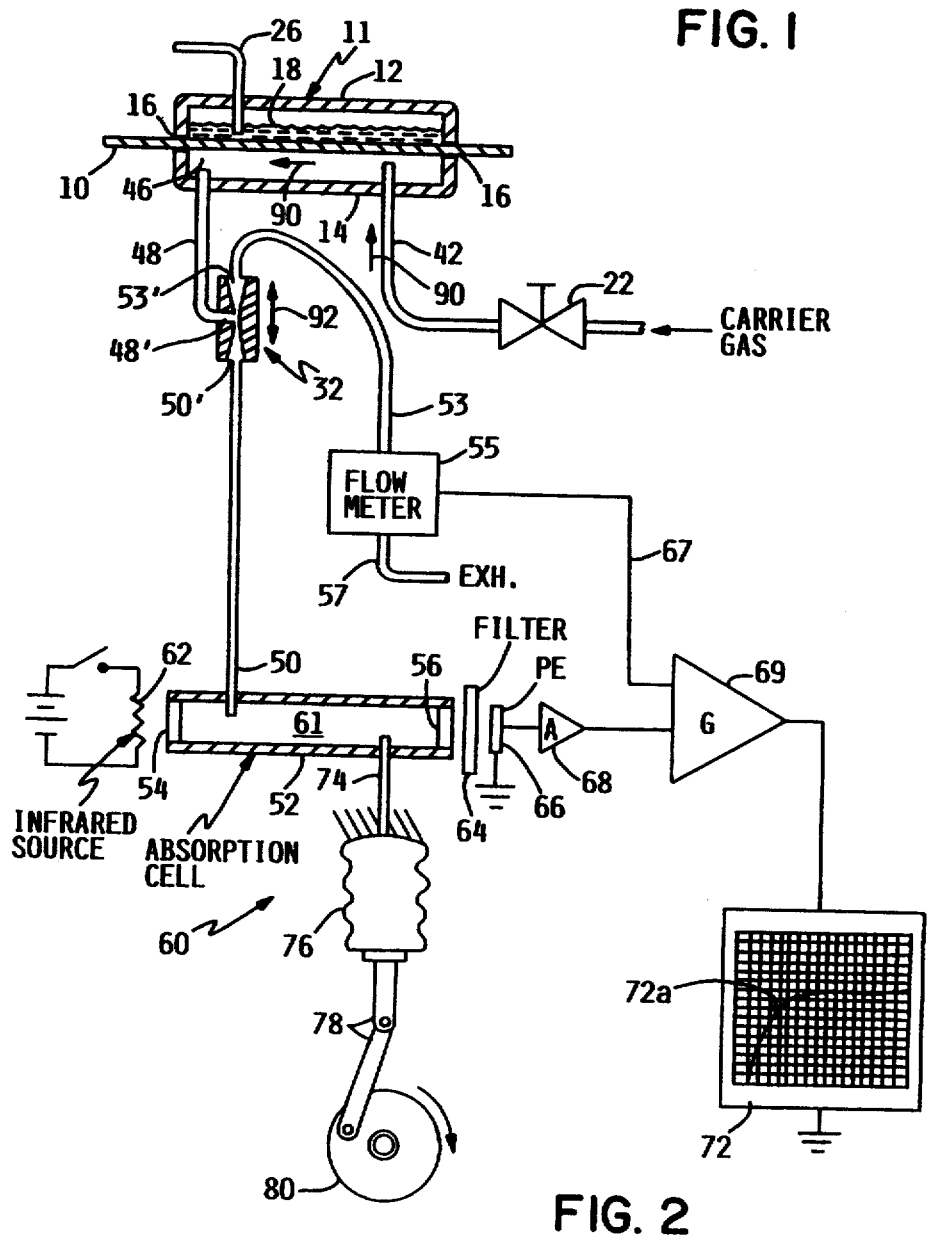
FIG. 2 shows a system and apparatus in which the measurement cell may be used.

Referring first to FIG. 2, a system and apparatus of the type disclosed in U.S. patent Ser. No. 08/126,921 is shown; the disclosure of this patent application is hereby incorporated by reference. A plastic film 10, such as polyethylene, Mylar or Saran, is clamped in a diffusion cell 11 composed of two separable halves, there being an upper casing 12 and a lower casing 14 appearing in cross-section in FIG. 2. The edges 16 of the casings 12 and 14 which abut against the plastic film 10 have soft rubber gaskets 6 extending therearound. By means of suitable clamps, such as C-clamps (not shown), the two casing halves 12, 14 are securely clamped together and against the film 10.

The upper casing 12 forms a cavity or chamber 18 into which a volume of water is introduced, using a damp sponge or via a tube 26. Upper chamber 18 has a sufficient quantity of water so as to provide a completely saturated chamber, one wall of which is formed by the film 10. A dry carrier gas such as nitrogen, helium or argon, or other type of inert gas, is conveyed under pressure into the lower chamber 46 of diffusion cell 11, via an adjustable metering valve 22 and tube 42. The gas flow direction is shown by the arrows 90; the carrier gas leaves chamber 46 via tube 48. Tube 48 extends from the diffusion cell chamber 46 to the center point of a venturi 32. One end of the venturi 32 is connected via tube 50 to absorption cell 52, and the other end of the venturi 32 is connected via tube 53 to a flow meter 55. One form of flow meter 55 which is particularly useful in connection with the present invention is a "micro-bridge mass air flow sensor", manufactured by the Microswitch Division of Honeywell. This air flow sensor provides actual mass flow sensing capabilities and is sensitive to flows in the rate 0–200 standard cubic centimeters per minute (sccm). It provides an analog output voltage representative of the sensed flow rate. The flow meter 55 operates on the theory of heat transfer due to mass air flow directed across the surface of a sensing element; the output voltage varies in proportion to the mass air or other gas flow through the inlet and outlet ports of the sensor. It is identified by the manufacturer as a micro-bridge AWM2000 series, developing an output voltage varying from 0–45 millivolts (mv), as the measured air flow varies from 0–200 sccm.

Absorption cell 52 forms a part of infrared gas analyzer 60, which also includes a source of infrared (IR) energy 62 positioned adjacent a window 54. The IR source 62 provides radiant energy that passes completely through the cell 52 and windows 54 and 56, and then through an interference filter 64 which is selected so as to transmit a narrow band of radiation centered near 2.6 microns, which is one of the wavelengths at which water vapor provides high attenuation of IR energy. The IR source 62 may generate radiation broadly over the IR spectrum from 0.76–200 microns, and the presence of water vapor will attenuate this radiation as certain narrow band segments of the overall wavelength. One of these attenuation segments lies at about 2.6 microns, which is why the interference filter 64 is selected to transmit radiation at this wavelength. Of course, other attenuation bands exist for water vapor within the IR spectrum, and other interference filters associated with these attenuation bands would also be suitably usable with the invention.

After passing through the filter 64 the radiation impinges upon a photoelectric cell 66. Photo cell 66 converts the impinging radiation into an electrical signal which is conveyed to an amplifier 68, where the electrical signal is suitably amplified. The output from amplifier 68 is conveyed to a variable gain amplifier "G" designated as 69, and the output from variable gain amplifier 69 is conveyed to a display device, such as a strip chart recorder 72. The gain of variable gain amplifier 69 is adjusted by a signal via line 67, which originates in flow meter 55. This signal is directly proportional to the volume flow rate of gas passing through flow meter 55, and outwardly through exhaust tube 57. The gain of amplifier 69 is inversely proportional to the signal conveyed via line 67; therefore, as the flow rate increases through flow meter 55 the gain of the output signal from IR gas analyzer 60 is correspondingly reduced.

The amount of gas flow through venturi 32 is determined by the action of a bellows 76, which creates an oscillatory pressure variation in absorption cell 52 and backward through tube 50. Because of this effect, the center tap of venturi 32 is inherently at a reduced pressure, thereby creating a net flow of the carrier gas and water vapor mixture within chamber 46 in the direction shown by arrows 90. This carrier gas and water vapor mixture will be drawn into the venturi center tap, and will diffuse through the tubes connected thereto and into the absorption cell 52.

Bellows 76 is driven by a linkage 78 connected to a rotatable drive mechanism 80 via a crank arm. The drive mechanism 80 rotates in the direction shown by the arrows, thereby creating a reciprocating action to drive bellows 76, and thereby creating gas pulsations via tube 74 into absorption cell 52.

A representative curve 72a shows the typical response of the strip chart recorder 72 to the detection of a predetermined amount of water vapor in cell 46 as a result of the operation of the invention. Curve 72a shows that the measured water vapor concentration will gradually rise to a stabilization level, and will thereafter remain relatively constant, depending upon the relative permeability of the water vapor through film 10. The stabilized portion of curve 72a then becomes representative of the permeability of the film 10.

It should be noted that the electrical functions illustrated in FIG. 2 can be equally well performed in a suitably programmed digital computer, wherein respective measurements are transformed into digital values which may then be coupled into the computer processor for calculations and other manipulations in order to produce the requisite drive signal for a suitable display apparatus.

Figure 1:
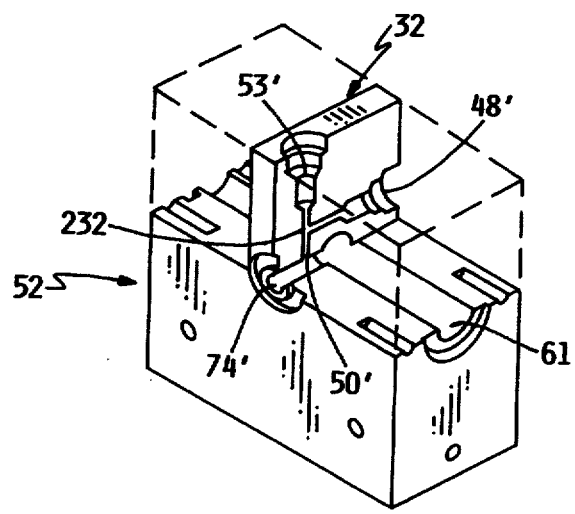
FIG. 1 shows an isometric view of the measurement cell of the present invention in partial breakaway.

FIG. 1 shows an isometric view of the venturi 32 and the absorption cell 52 in the preferred embodiment used in conjunction with this invention. Absorption cell 52 is preferably formed in a metallic block 200 by drilling a passage therethrough to form a chamber 61. Chamber 61 is formed by boring through the entire longitudinal length of the block 200. Venturi 32 is also formed in metallic block 200 by drilling and cross-drilling several passages. These passages are represented in FIG. 2 as entry points for the tubes, and it is to be understood that the passage 50' shown in FIG. 1 functions in the same manner as the passage 50' and the tube 50 shown in FIG. 2. For example, a passage 53' is drilled from a top opening downwardly to intersect with a passage 48'. Passage 74' is representative of and equivalent to the tube 74 shown in FIG. 2, which connects between the bellows 76 and the absorption cell 52. Passage 50' connects between passage 74' and passages 53' and 48'. Passage 48' is cross-drilled to intersect passage 50' and passage 53' at their juncture. The intersection point 232 is functionally equivalent to the center intersection of venturi 32, and passage 48' connects to tube 48, and passage 53' connects to tube 53. It should be noted that passage 50' of FIG. 1 actually intersects passage 74'; whereas, in FIG. 2 tube 50 is shown as entering absorption cell 52, at a point separated from the entry point of tube 74. The passage 50' in FIG. 1 is functionally equivalent to the diagrammatic representation of FIG. 2, even though the passage 50' is drilled into passage 74'. The point of entry of passage 50' is sufficiently close to chamber 61 so as to provide this functional equivalence.

Figure 3:
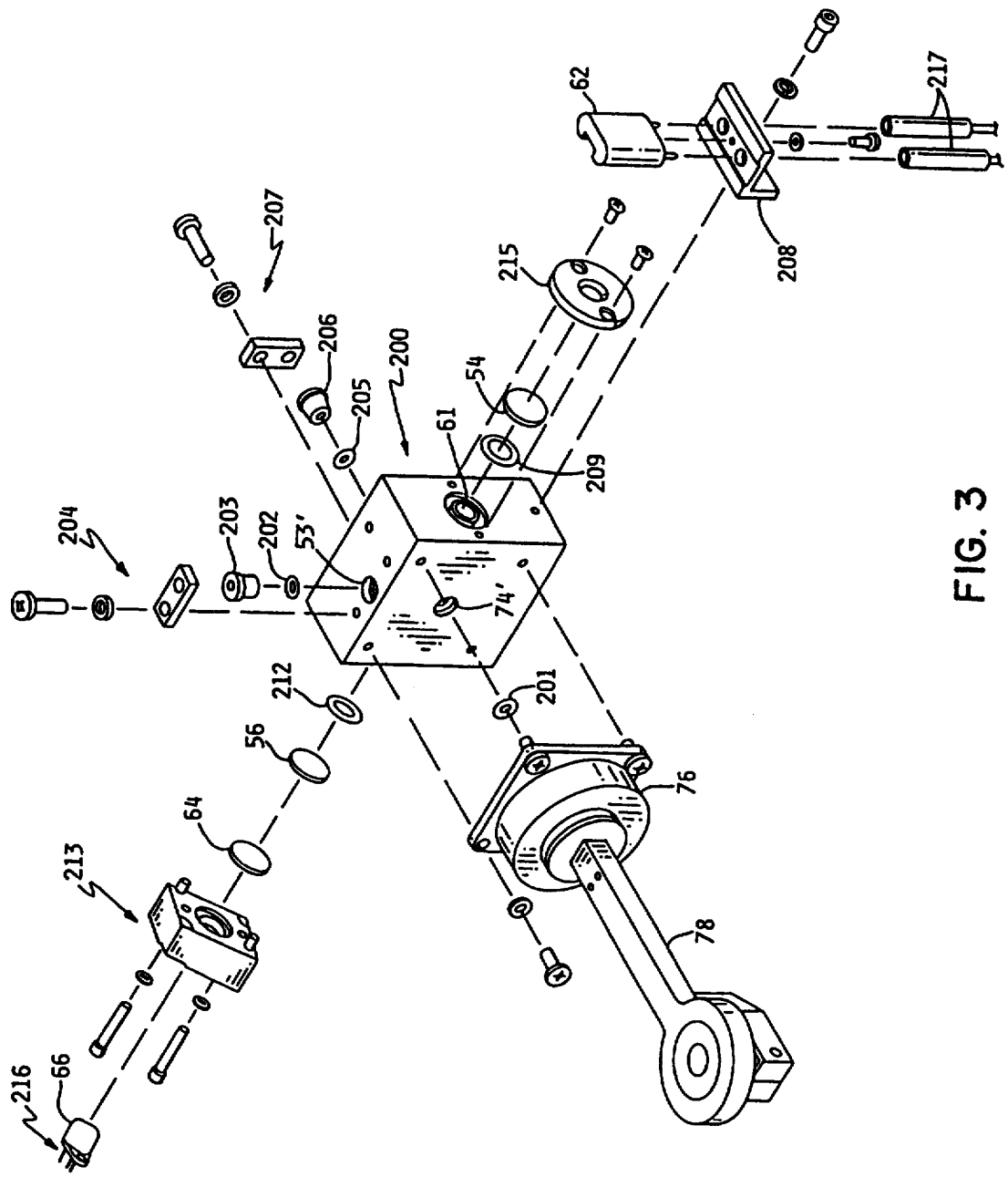
FIG. 3 shows an exploded view of the measurement cell.

FIG. 3 shows an exploded diagram illustrating the metallic block 200 and the various component parts which are affixed thereto. Bellows 76 is affixed along one side of metallic block 200, over the passage 74'. An O-ring seal 201 is sized to fit into the opening of passage 74' to ensure an airtight flow path from bellows 76 to passage 74'. Passage 53' receives an O-ring 202 and a tube connector 203 which is adapted for connecting to a suitable tube to run to flow meter 55. These items are secured against the outside of metallic block 200 by means of fasteners 204. Similarly, passage 48' receives an O-ring 205 and a tubular connector 206 for securing to a tubular segment to connect to the diffusion cell 11. Fasteners 207 are used to affix these connections to the side of metallic block 200.

Infrared source 62 and its electrical connectors 217 are affixed adjacent one end of chamber 61 by mounting hardware and housing 208. A window 54 is clamped against an O-ring 209 and between housing 208 and the opening into chamber 61 by a mounting bracket 215. The other opening into chamber 61 receives a window 56 and filter 64 which are secured against the end of chamber 61 via an O-ring 212 by a mounting bracket 213. A photocell 66 is attachable to the mounting bracket 213, and electrical connectors 216 convey the electrical signals from photocell 66 to amplifier 68.

Figure 4:
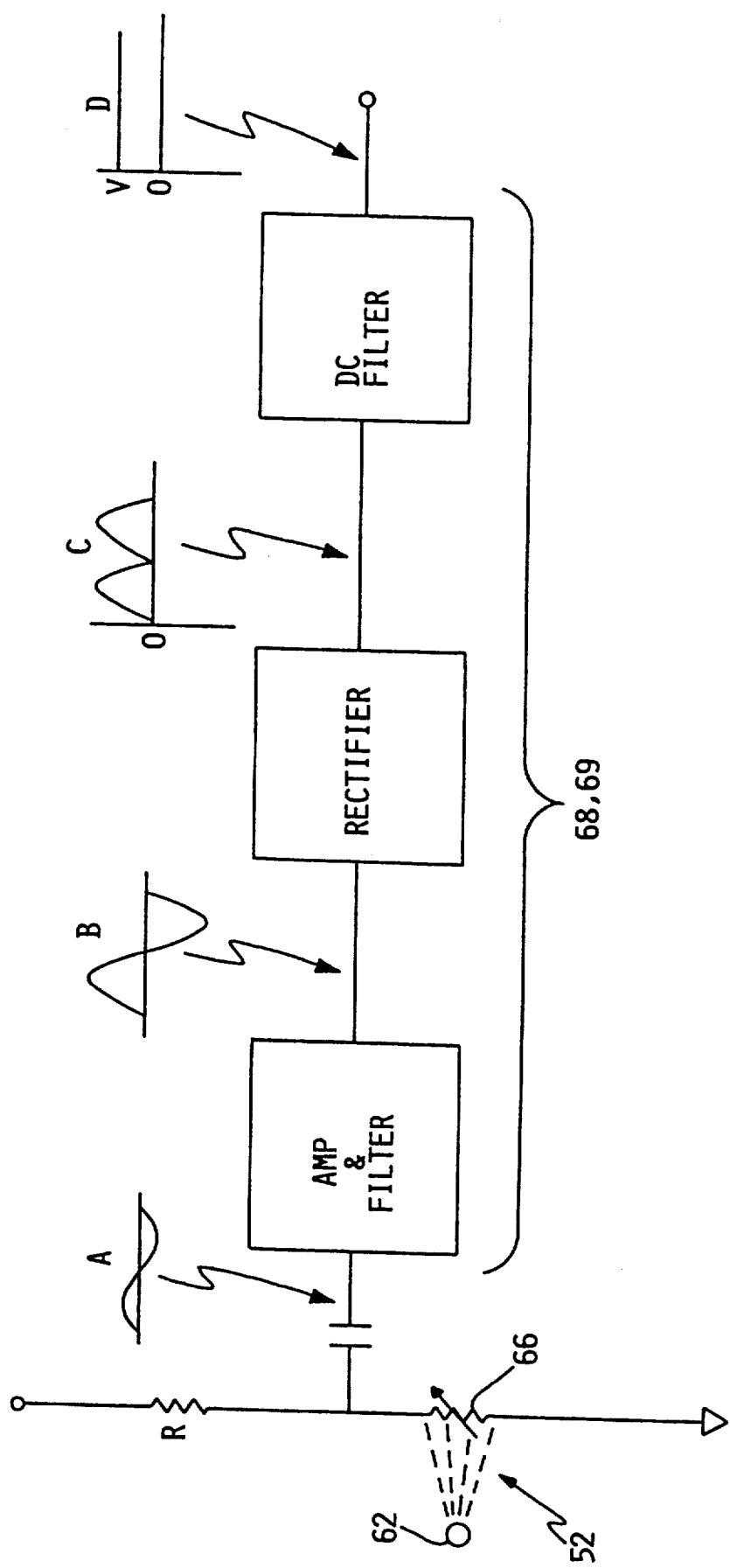
FIG. 4 shows a representative electrical diagram illustrating the signals produced by the invention.

FIG. 4 shows a representative electrical diagram to illustrate the relative electrical signals which are produced as a result of radiation from infrared source 62 passing through absorption cell 52 and causing a corresponding signal to be received by photocell 66. The signal from photocell 66 is passed through the amplifier and gain circuit 68, 69 in the functional representations of FIG. 4; i.e., the input radiation signal A is amplified and filtered to produce a filtered signal B; this signal is rectified to produce a rectified DC signal C, and the rectified signal is filtered to produce a constant DC voltage level signal D. The relative DC voltage "V" is representative of the radiation received by the photocell 66 and is therefore representative of the water vapor concentration within absorption cell 52.

The photocell signal A is a composite signal which includes various components attributable to the radiation from source 62, the transmissivity of the optical components 54, 56 and 64, the heating effects of block 200, the reflectance within chamber 61, and the oscillatory effects of bellows 76. The effects of bellows 76 are two-fold: The bellows typically cycles at a frequency of 30 cycles per second (cps) which produces compression energy variations in absorption cell 52 corresponding to this rate, and the operation of the bellows 76 also produces mechanical vibration of the entire block 200 which is believed to affect the composite radiation signal passing through absorption cell 52. It is difficult to define all of the signal components which produce the photocell voltage A, and it is impossible to specifically measure each of these components; however, empirical testing under a number of different conditions enables one to define an overall "noise" component of the radiation signal which is a composite value of all of the contributing "noise" factors and to infer this "noise" signal composite as distinct from the desired water vapor concentration signal.

Figure 5A:
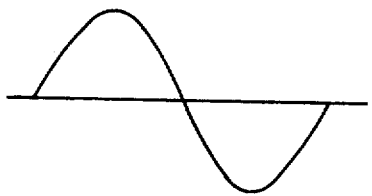
FIG. 5A shows a prior art representation of the compression energy produced by bellows 76.
Figure 5B:
FIG. 5B shows a prior art representation of the radiant energy produced within the absorption cell.

FIG. 5A shows a representation of the compression energy which is imparted into absorption cell 52 by action of bellows 76; FIG. 5B shows a representation of the radiation "noise" energy which can be inferred from empirical testing of the absorption cell and which is attributable to all of the known and unknown factors affecting radiation. It is important to note that the "noise" energy of FIG. 5B is always out of phase with the compression energy of FIG. 5A.

Figure 5C:
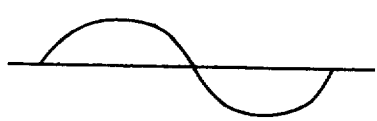
FIG. 5C shows a prior art resultant signal based respectively on the FIGS. 5A–5B.
Figure 5D:
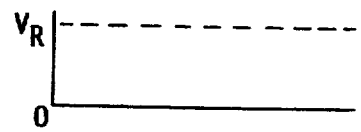
FIG. 5D shows the prior art corresponding DC signal corresponding respectively to FIGS. 5C.

FIG. 5C shows the radiation signal which is produced as a composite result of the energy effects shown in FIGS. 5A and 5B, under dry gas conditions flowing into the absorption cell. This corresponds to the signal A which is illustrated in FIG. 4. FIG. 5D shows the resultant DC voltage $V_R$ which is produced by the circuits of FIG. 4 as a result of the radiation signal of FIG. 5C; this corresponds to the signal D illustrated in FIG. 4 under dry gas conditions. Therefore, the voltage $V_R$ can be thought of as a base line reference voltage which is indicative of zero water vapor concentration, and all subsequent water vapor concentrations can be referenced to this voltage level. The representations of FIGS. 5A-5D are indicative of conditions observed and measured with respect to the prior art instruments wherein the dry air radiation signal of FIG. 5C is "in phase" with the compression energy signal of FIG. 5A, and is "out of phase" with the radiation signal representation of FIG. 5B. The DC voltage signal $V_R$ of FIG. 5D is representative of the dry air base line voltage measured with prior art instruments; it should be noted that the reference voltage $V_R$ will always be a positive voltage, irrespective of the relative "phases" of the waveforms of FIGS. 5A-5C, because the circuitry illustrated in FIG. 4 rectifies the radiation signal and always produces a positive voltage D corresponding to the average value of the rectified signal.

Figure 6A:
FIGS. 6A and 6B, show representative prior art radiation signals resulting from a first water vapor concentration in the absorption cell.
Figure 6B:
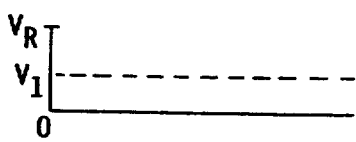

FIGS. 6A-6F show radiation signals and resultant DC voltages corresponding to three different measured water vapor concentrations in the absorption cell, under the prior art conditions shown in FIGS. 5A-5D. FIG. 6A shows the radiation signal resulting from a first low water vapor concentration, and the DC voltage $V_1$ of FIG. 6B shows the resultant output voltage. It should be noted that the voltage $V_1$ is at a lower level than the voltage $V_R$, which infers a negative-going transfer characteristic; i.e., the dry air voltage $V_R$ is at a higher level than the first water vapor concentration signal $V_1$.

Figure 6C:
FIGS. 6C and 6D, show representative prior art radiation signals resulting from a second water vapor concentration in the absorption cell.
Figure 6D:
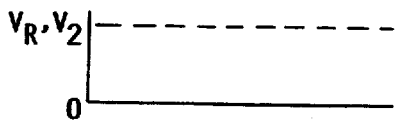

FIG. 6C shows a radiation signal corresponding to a second water vapor concentration in the absorption cell, and this produces a second output DC voltage $V_2$ as shown in FIG. 6D. The second water vapor concentration voltage level $V_2$ is exactly equal to the dry air voltage reference $V_R$, which results because the radiation signal of FIG. 6C is identical in peak value to the radiation signal of FIG. 5C, but is 180° out of phase. Therefore, it is apparent that the prior art results in a nonlinearity wherein increasing levels of water vapor concentration will be detected as apparently drier conditions when referenced to the voltage $V_R$.

Figure 6E:
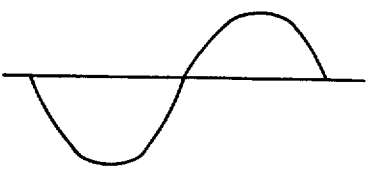
FIGS. 6E and 6F, show representative prior art radiation signals resulting from a third water vapor concentration in the absorption cell.
Figure 6F:
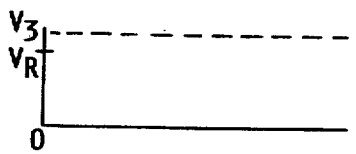

FIG. 6E shows the radiation signal resulting from a third and higher water vapor concentration. This produces the DC output voltage of FIG. 6F, i.e., $V_3$. Since the peak value of the signal of FIG. 6E is greater than the peak value of the voltage of FIG. 5C, the DC voltage $V_3$ appears to be at a higher level than the reference voltage $V_R$, thereby compounding the nonlinearity problem.

Figure 7:
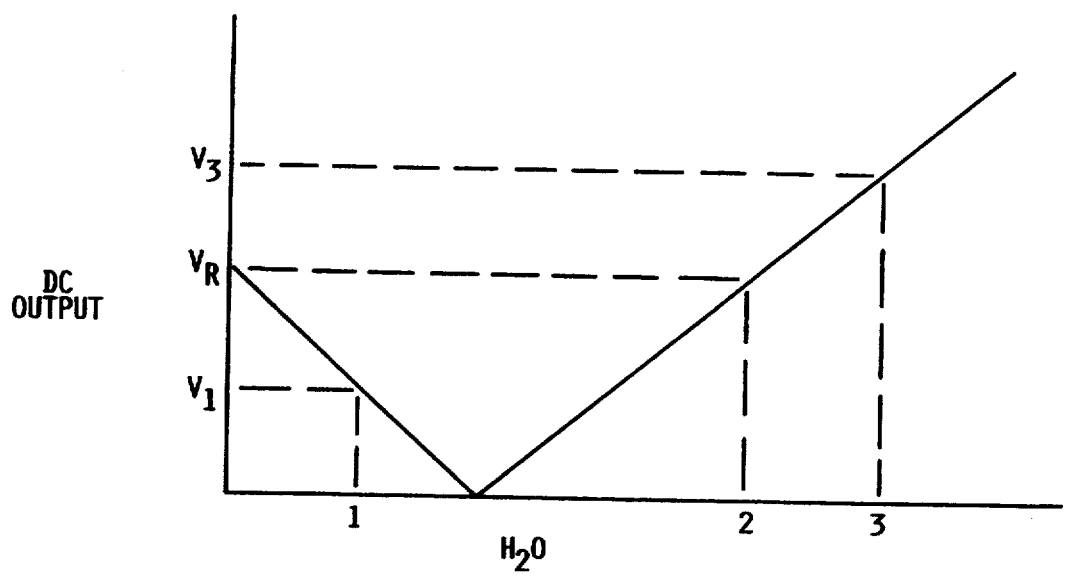
FIG. 7 shows the transfer characteristic of a system having the characteristics illustrated by FIGS. 6A–6F.

FIG. 7 shows the transfer function characteristic corresponding to the prior art, and illustrative of the waveforms of FIGS. 5A-5D and 6A-6F. It is apparent that the voltage $V_1$, representative of a lower water vapor concentration, produces a reduced DC output voltage signal than the dry gas equivalent voltage $V_R$. The voltage $V_1$ corresponds to a water vapor concentration level (1) as shown on the X-axis of FIG. 7. It is also apparent that the water vapor concentration (2) shown on FIG. 7 yields an output voltage $V_2$ which is equal to $V_R$. Finally, the highest water vapor concentration (3), as shown on FIG. 7, produces a higher output voltage $V_3$, which is greater than $V_R$. The inherent nonlinearity of the output voltages at water vapor levels at or below (2) renders the instrument unusable for water vapor concentrations below this minimum level. The instrument may be used for measuring water vapor concentrations greater than concentration (2), for the curve of FIG. 7 becomes linear above this point.

Figure 8A:
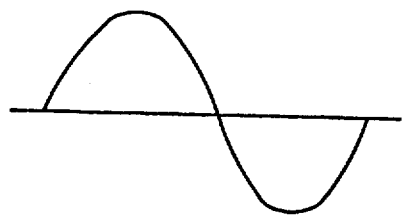
FIG. 8A shows a representation of the compression energy produced by bellows 76.
Figure 8B:
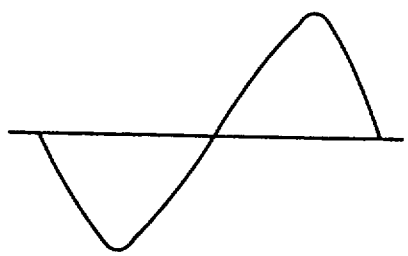
FIG. 8B shows a representation of the radiant energy produced within the absorption cell.
Figure 8C:
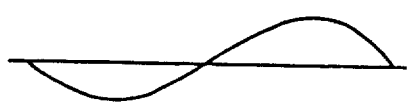
FIG. 8C shows resultant signals based respectively on the FIGS. 8A–8B.
Figure 8D:
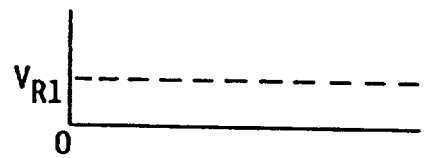
FIG. 8D shows the corresponding DC signals corresponding to FIG. 8D.
Figure 9A:
FIGS. 9A and 9B show representative radiation signals resulting from a first water vapor concentration in the absorption cell.
Figure 9B:
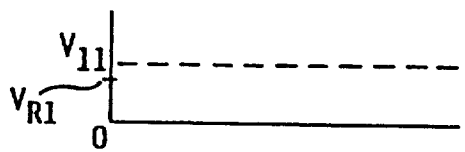
Figure 9C:
FIGS. 9C and 9D show representative radiation signals resulting from a second water vapor concentration in the absorption cell.
Figure 9D:
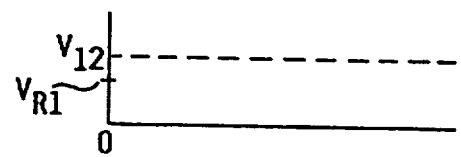
Figure 9E:
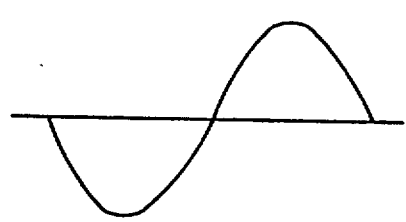
FIGS. 9E and 9F show representative radiation signal resulting from a third water vapor concentration in the absorption cell.
Figure 9F:
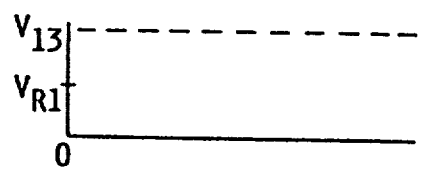
Figure 10:
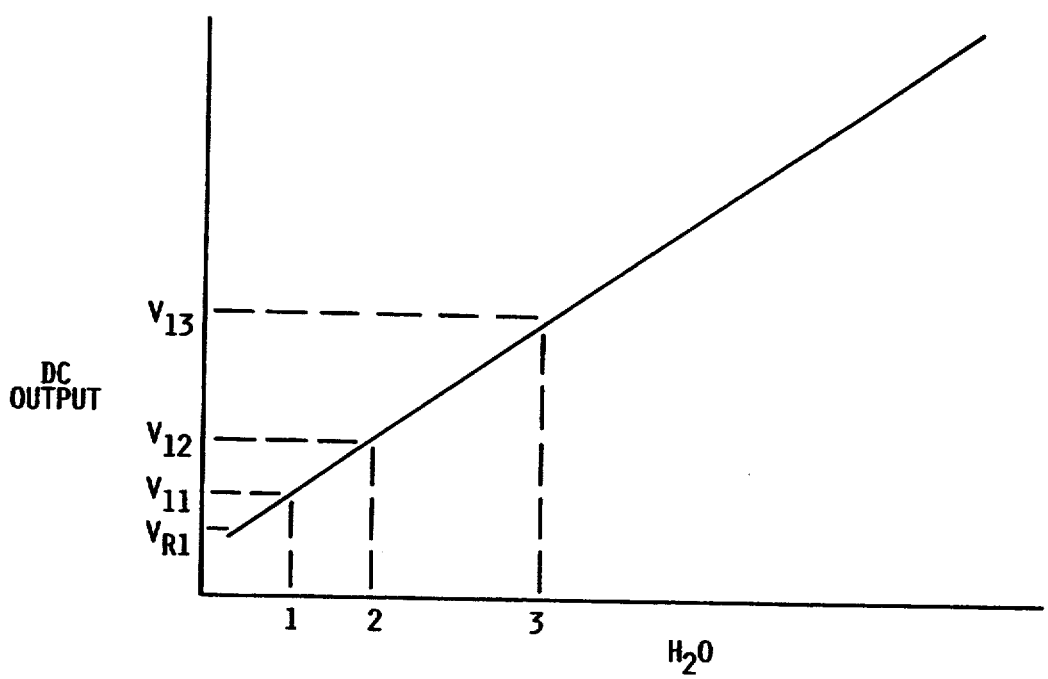
FIG. 10 shows the transfer characteristic of the system illustrated by the waveforms of FIGS. 9A–9F.

FIGS. 8A-8D, and FIGS. 9A-9F, and the transfer function shown in FIG. 10, are all representative of the types of results which are achieved with the present invention. Referring first to FIG. 8A, there is shown the same compression energy waveform as is shown in FIG. 5A. FIG. 8B shows the radiation energy waveform which is similar in "phase" to the waveform of FIG. 5B, but which is selected to have a peak amplitude greater than the energy waveform of FIG. 8A. This selection results in a dry gas radiation signal, as shown in FIG. 8C, which is always in "phase" with the radiation energy waveform of FIG. 8B, and therefore produces a DC output voltage $V_{R1}$ as shown in FIG. 8D.

FIGS. 9A-9C and 9E show the radiation signals corresponding to the same water vapor concentrations as are represented in FIGS. 6A, 6C and 6E; i.e., increasingly heavier concentrations of water vapor. FIG. 9B shows a DC output voltage $V_{11}$ which is produced as a result of receiving the radiation signal of FIG. 9A. It should be noted that voltage $V_{11}$ is slightly greater than the reference voltage $V_{R1}$, and the difference between these two voltages is indicative of the water vapor concentration level in the absorption cell. FIG. 9C shows a water vapor concentration level (2), and FIG. 9D shows the DC output voltage resulting therefrom. This DC output voltage $V_{12}$ is greater than the dry gas reference voltage $V_{R1}$, and is also greater than the DC output voltage $V_{11}$, which is representative of an increased water vapor concentration level (2). FIG. 9E shows a still greater water vapor concentration level (3) and the graph of FIG. 9F shows the DC output voltage $V_{13}$ resulting therefrom. Voltage $V_{13}$ is greater than the reference voltage $V_{R1}$, and is greater than the DC output voltage $V_{11}$, and is greater than the DC output voltage $V_{12}$, and is representative of a still greater water vapor concentration level in the absorption cell. FIG. 10 shows a transfer characteristic of the present invention, illustrating the respective DC output voltages of FIGS. 8D, 9B, 9D, 9F and the water vapor concentration levels corresponding thereto. It is apparent that increasing levels of water vapor concentration result in a linear increase in the respective output voltages, down to the reference level of $V_{R1}$.

Stated in general principles, the present invention controllably regulates the radiation energy transfer characteristics within the absorption cell such that the dry gas radiation signal is always in phase with the water vapor radiation signal produced by any water vapor concentration level which is desired to be measured by the instrument. This is apparent from a comparison of the respective phases of the waveforms of FIGS. 8C, 9A, 9C and 9E. This principle produces a linearly varying DC output voltage level which is proportionate to the water vapor concentration level in the absorption cell.

It has been found that the performance of absorption cell 52 is dramatically affected by the relative smoothness of the interior walls of chamber 61. If chamber 61 is formed by a drilling tool, and is subsequently polished, the walls of chamber 61 will typically have a surface roughness on the order of 2-10 microinches, which is measured as the difference between the high and low surface irregularities. Under these circumstances, it is believed that the radiation generated by the IR source 62 is reflected to a significant degree from the chamber 61 wall surfaces prior to exiting from chamber 61 via window 56. This radiation reflectance apparently contributes to some of the radiation "noise" signal variations which are caused by the operation of bellows 76 and, therefore, can be considered as "radiation noise" generated within chamber 61. It has been found that a roughening of the interior wall surface of chamber 61 provides a technique for controlling this "noise" radiation by apparently reducing the reflectance from the walls of chamber 61 and/or increasing the heating effects of the absorption cell and will result in linear response from photocell 66, corresponding to the desired water vapor concentrations in the absorption cell. The "noise" signal can readily be measured by operating the apparatus under dry carrier gas conditions and by measuring the electrical signal from photocell 66 under these conditions.

Testing has shown that the marked improvement in overall linearity is achievable when the wall surface area of chamber 61 is roughened to at least 15 microinches and preferably to a surface roughness in the range of 15–70 microinches. This has resulted in at least an order of magnitude improvement in the linearity of the apparatus and has enabled the apparatus to make accurate permeability measurements of a wider range of materials which are available for testing. For example, with the surface of the walls of chamber 61 in polished or unroughened condition the apparatus has been tested to a level of about 5 grams per square meter per day in measuring water vapor permeability through Mylar film. By contrast, when the walls of chamber 61 are roughened to at least 15 microinches the improved linearity of the instrument provides an accurate measurement of water vapor permeability down to the range of 0.001 grams per square meter per day when measuring coated film. This remarkable improvement is thought to be attributable entirely to the degree of linearity improvement caused by controlling the surface roughness in chamber 61.

It has been found that increasing the surface roughness of the wall surface of chamber 61 beyond about 70 microinches actually reduces the usability range of the instrument. The effect of this increased surface roughness is to raise the "zero" reference level for the DC output voltage, thereby to obscure small voltage changes about the zero point. It is important to keep the zero reference point below about 100 millivolts, in order to provide an adequate voltage resolution for discriminating small changes in permeability. For example, testing of the instrument at extremely low permeability rates shows a variation of about 12 mv/gm/M$^2$/day under conditions of relatively high gas flow through the absorption cell. At very low flow rates and low permeability testing, measurements of 0.125 millivolts have been measured corresponding to 0.001 gm/M$^2$/day. These exceedingly small millivolt variations are difficult to identify unless the zero point voltage is kept below about 100 millivolts.

The foregoing tests have shown that regulation of the radiation energy within the absorption cell greatly affects the linearity of the transfer function relating to the radiation signals derived from the sensor. These tests have also shown that the radiation energy within the absorption cell may be regulated by controlling the surface roughness of the cell walls such that the radiation signal produced by dry gas within the cell varies in time phase coincidence with radiation signals produced by any reasonable water vapor concentration level in the gas. This phasing relationship provides a standard of measurement to evaluate the degree of regulation required for any particular cell.

It is believed that other forms of radiation energy regulation may also be suitably employed in particular cell constructions. For example, the interior diameter and overall length of the absorption cell is believed to be a factor which influences interior cell radiation levels, and in proper situations it may be effective to coat all or a portion of the interior cell surface with a black coloring, i.e., to produce a black-body effect within the absorption cell. Another effective control over interior cell radiation effects may be utilization of a threaded member which can be selectively introduced into the cell interior for the purpose of modifying the internal cell radiation characteristics. Such a threaded member may be coated in black coloring to enhance the influence over radiation energy effects in the interior of the absorption cell. Other and further devices may be appropriate in particular situations wherein the desired observed result is time-varying coincidence with radiation signals produced by dry gas and radiation signals produced by gases having water vapor concentrations.

In operation, the DC output voltage corresponding to a dry gas operation may be recorded, and compared with the DC output voltage of at least two test samples of known permeability, wherein the test samples are known to have a permeability at least below the permeability range where it is desired to operate. The instrument is tested to ensure that the DC output voltages are consistently measured according to the arrangements of FIGS. 8D, 9B, 9D and 9F, thereby assuring a transfer function of the type shown in FIG. 10. If the desired linearity is not achieved an adjustment in the relative surface roughness of the absorption cell may be required until the desired transfer characteristic is achieved. Other and further modifications may be possible to achieve the desired linear transfer function characteristic, but adjustment of surface roughness of the absorption cell has been found to achieve satisfactory results with the present invention.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. An apparatus for measuring dry gas samples and water vapor gas samples in a test cell having a gas chamber, comprising:
   a) a cyclical means for periodically pressurizing gas in said chamber;
   b) a pair of windows, one on either end of said chamber, thereby to provide a radiation path through said chamber;
   c) a radiation source outside said chamber adjacent one of said windows, and a radiation detector outside said chamber adjacent the other of said windows, said radiation detector having means for producing electrical signals as a result of receiving radiation from said radiation source, said electrical signals having a periodic waveform influenced by said means for periodically pressurizing gas in said chamber;

d) means for regulating the radiation energy transfer characteristics of said chamber; and e) means for adjusting said means for regulating whereby a radiation signal produced by a dry gas in said chamber is time variant in the same phase as a radiation signal produced by a gas having a water vapor concentration in said chamber.

2. The apparatus of claim 1, wherein said radiation source radiates infrared radiation energy, and said radiation detector is responsive to said infrared radiation energy.

3. The apparatus of claim 2, wherein said cyclical means for periodically pressurizing gas operates at a frequency of about 30 cycles per second.

4. The apparatus of claim 2, wherein said means for regulating the radiation energy transfer characteristics comprises controlling the surface roughness of the walls of said chamber.

5. The apparatus of claim 4, wherein said means for adjusting said means for regulating comprises varying the surface roughness of the walls of said chamber.

6. The apparatus of claim 5, wherein said means for adjusting is variable over the range of 15 to 70 microinches of surface roughness.

7. The apparatus of claim 6, further comprising at least one filter adjacent one of said pair of windows, said filter having means for passing radiation at a wavelength of about 2.6 microns.

8. The apparatus of claim 6, wherein said chamber comprises a bore through a metallic block.

9. The apparatus of claim 8, wherein each of said pair of windows is clamped against said block over said bore.

10. The apparatus of claim 9, further comprising gas passages in said block between said bore and said means for periodically pressurizing gas.

11. An apparatus for measuring dry gas and water vapor concentrations in a test cell having a gas chamber, comprising:

a) a cyclical compressor connected to said chamber and having means for periodically pressurizing the gas in said chamber;

b) a pair of windows, one on either side of said chamber, thereby to provide a radiation path through said chamber;

c) a radiation source outside said chamber adjacent one of said windows, and a radiation detector outside said chamber adjacent the other of said windows, said radiation detector having means for producing electrical signals as a result of receiving radiation from said radiation source; and d) said chamber having interior walls roughened to a sufficient degree so as to obtain from said radiation detector a dry gas signal which is in phase with all water vapor signals.

12. The apparatus of claim 11, wherein said radiation source has means for radiating IR energy, and said radiation detector is responsive to said IR energy.

13. The apparatus of claim 12, wherein said cyclical compressor means for periodically pressurizing operates at about 30 cycles per second.

14. The apparatus of claim 11, wherein said chamber further comprises an elongated bore through a metallic block.

15. The apparatus of claim 11, wherein said chamber interior walls are roughened to between 15 and 70 microinches of surface roughness.

16. The apparatus of claim 14, wherein said respective windows are clamped against said block over said bore.

17. The apparatus of claim 16, further comprising at least one filter adjacent one of said windows, said filter having means for passing radiation at substantially 2.6 microns.

18. The apparatus of claim 14, further comprising gas passages in said metallic block coupled between said bore and said means for periodically pressurizing the gas.

19. The apparatus of claim 18, wherein said cyclical compressor having means for periodically pressurizing further comprises a mechanically actuated bellows.

20. The apparatus of claim 19, further comprising passages in said metallic block connected between said bore and a means for supplying said gas.

21. In an apparatus for measuring gas concentrations in a gas chamber having interior gas chamber walls, the improvement comprising gas chamber walls roughened to between 15 and 70 microinches.

22. An apparatus for measuring gas concentrations in a chamber having infrared energy passing therethrough, comprising:

a) a source of infrared energy positioned proximate said chamber;

b) said chamber having windows affixed proximate respective opposite ends positioned to receive and pass said infrared energy;

c) an infrared detector positioned proximate one of said windows at a chamber end opposite to the position of said infrared source;

d) said chamber having interior walls roughened to between 15 and 70 microinches;

e) a metallic block enclosing said chamber and tightly sealed to said windows; and f) means for alternately compressing and decompressing gas in said chamber.

* * * * *